US008262557B2

(12) United States Patent
Chapman et al.

(10) Patent No.: US 8,262,557 B2
(45) Date of Patent: Sep. 11, 2012

(54) METHOD AND APPARATUS FOR LEVATOR DISTENSION REPAIR

(75) Inventors: Kelly Ann Chapman, Minnetonka, MN (US); Matthew J. Olson, Minnetonka, MN (US); Alton V. Hallum, III, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 767 days.

(21) Appl. No.: 12/308,083

(22) PCT Filed: Jun. 8, 2007

(86) PCT No.: PCT/US2007/070732
§ 371 (c)(1),
(2), (4) Date: Apr. 10, 2009

(87) PCT Pub. No.: WO2007/146784
PCT Pub. Date: Dec. 21, 2007

(65) Prior Publication Data
US 2010/0152528 A1  Jun. 17, 2010

Related U.S. Application Data

(60) Provisional application No. 60/811,790, filed on Jun. 8, 2006, provisional application No. 60/825,357, filed on Sep. 12, 2006.

(51) Int. Cl.
*A61F 2/00* (2006.01)
(52) U.S. Cl. .............................................. 600/37; 600/30
(58) Field of Classification Search ....................... 600/37
See application file for complete search history.

(56) References Cited

U.S. PATENT DOCUMENTS

| 4,741,330 | A | | 5/1988 | Hayhurst |
| 5,263,969 | A | * | 11/1993 | Phillips .......................... 606/213 |
| 5,368,602 | A | | 11/1994 | De La Torre |
| 5,464,403 | A | * | 11/1995 | Kieturakis et al. ................ 606/1 |
| 5,647,836 | A | | 7/1997 | Blake, III et al. |
| 5,824,041 | A | * | 10/1998 | Lenker et al. .................. 606/195 |
| 5,840,011 | A | | 11/1998 | Landgrebe et al. |
| 6,042,534 | A | * | 3/2000 | Gellman et al. ................. 600/30 |
| 6,669,735 | B1 | | 12/2003 | Pelissier |
| 6,689,047 | B2 | * | 2/2004 | Gellman ........................ 600/30 |
| 7,975,698 | B2 | * | 7/2011 | Browning ..................... 128/834 |
| 2003/0212305 | A1 | | 11/2003 | Anderson et al. |
| 2003/0220538 | A1 | * | 11/2003 | Jacquetin ........................ 600/37 |
| 2004/0193211 | A1 | * | 9/2004 | Voegele et al. ................ 606/205 |
| 2005/0283189 | A1 | * | 12/2005 | Rosenblatt .................... 606/216 |
| 2006/0025649 | A1 | | 2/2006 | Smith et al. |
| 2006/0195011 | A1 | | 8/2006 | Arnal et al. |
| 2006/0224038 | A1 | | 10/2006 | Rao |
| 2007/0062541 | A1 | | 3/2007 | Zhou et al. |

(Continued)

FOREIGN PATENT DOCUMENTS

EP  1600118 A1  11/2005

(Continued)

*Primary Examiner* — Patricia Bianco
*Assistant Examiner* — Raymond E Harris
(74) *Attorney, Agent, or Firm* — Kimberly K. Baxter; Gregory L. Koeller

(57) ABSTRACT

Improved methods and apparatuses for treatment of pelvic organ prolapse are provided. A specialized mesh having a shape for convenient subcutaneous placement to support the levator ani muscles is provided, as is a method of use of such a device. Appropriate devices for introducing such a mesh implant are also disclosed.

14 Claims, 8 Drawing Sheets

U.S. PATENT DOCUMENTS

| | | |
|---|---|---|
| 2008/0021265 A1 | 1/2008 | Garbin et al. |
| 2008/0027271 A1 | 1/2008 | Maccarone |
| 2008/0045782 A1 | 2/2008 | Jimenez |
| 2010/0105979 A1 | 4/2010 | Hamel et al. |
| 2010/0261952 A1 | 10/2010 | Monetpetit et al. |

FOREIGN PATENT DOCUMENTS

| | | | |
|---|---|---|---|
| EP | 1609439 A1 | 12/2005 | |
| WO | WO03073960 A1 | 9/2003 | |
| WO | WO03077772 A1 | 9/2003 | |
| WO | WO03096929 A1 | 11/2003 | |
| WO | WO2004045457 A1 | 6/2004 | |
| WO | WO2005/112842 | * | 5/2005 |
| WO | WO2005110274 A1 | 11/2005 | |
| WO | WO2006/069078 | * | 6/2006 |
| WO | WO2006069078 A2 | 6/2006 | |
| WO | WO2007059368 A1 | 5/2007 | |
| WO | WO2007081954 A1 | 7/2007 | |
| WO | WO2007081955 A1 | 7/2007 | |
| WO | WO2007146784 A2 | 12/2007 | |
| WO | WO2007149348 A2 | 12/2007 | |
| WO | WO2008013867 A1 | 1/2008 | |
| WO | WO2008015722 A1 | 2/2008 | |
| WO | WO2008042438 A2 | 4/2008 | |
| WO | WO2008057269 A1 | 5/2008 | |
| WO | WO2008083394 A2 | 7/2008 | |
| WO | WO2008124056 A1 | 10/2008 | |
| WO | WO2009005714 A2 | 1/2009 | |
| WO | WO2009011852 A1 | 1/2009 | |
| WO | WO2009038781 A1 | 3/2009 | |
| WO | WO2009075800 A1 | 6/2009 | |
| WO | WO2009145911 A1 | 12/2009 | |
| WO | WO2010129331 A2 | 11/2010 | |

* cited by examiner

METHOD AND APPARATUS FOR LEVATOR DISTENSION REPAIR

PRIORITY

This application claims benefit from International Application No. PCT/US2007/070732, having PCT Publication No. WO 2007/146784, which was filed on 8 Jun. 2007, which in turn claims priority under 35 USC §119(e) to U.S. Provisional Application Ser. No. 60/811,790, filed 8 Jun. 2006 and to U.S. Provisional Application Ser. No. 60/825,357, filed 12 Sep. 2006, the entire content of each application being incorporated herein by reference.

BACKGROUND OF THE INVENTION

1. Field of the Invention

This invention relates to urogenital surgery.

2. Description of the Related Art

Female genital prolapse has long plagued women. It is estimated by the U.S. National Center for Health Statistics that 247,000 operations for genital prolapse were performed in 1998. With the increasing age of the U.S. population, these problems will likely assume additional importance.

The common clinical symptoms of vaginal prolapse are related to the fact that, following hysterectomy, the vagina is inappropriately serving the role of a structural layer between intra-abdominal pressure and atmospheric pressure. This pressure differential puts tension on the supporting structures of the vagina, causing a "dragging feeling" where the tissues connect to the pelvic wall or a sacral backache due to traction on the uterosacral ligaments. Exposure of the moist vaginal walls leads to a feeling of perineal wetness and can lead to ulceration of the exposed vaginal wall. Vaginal prolapse may also result in loss of urethral support due to displacement of the normal structural relationship, resulting in stress urinary incontinence. Certain disruptions of the normal structural relationships can result in urinary retention, as well. Stretching of the bladder base is associated with vaginal prolapse and can result in complaints of increased urinary urgency and frequency. Other symptoms, such as anal incontinence and related bowel symptoms, and sexual dysfunction are also frequently seen with vaginal prolapse.

Anterior vaginal wall prolapse causes the vaginal wall to fail to hold the bladder in place. This condition, in which the bladder sags or drops into the vagina, is termed a cystocele. There are two types of cystocele caused by anterior vaginal wall prolapse. Paravaginal defect is caused by weakness in the lateral supports (pubourethral ligaments and attachment of the bladder to the endopelvic fascia); central defect is caused by weakness in the central supports. There may also be a transverse defect, causing cystocele across the vagina.

Posterior vaginal wall prolapse results in descent of the rectum into the vagina, often termed a rectocele, or the presence of small intestine in a hernia sac between the rectum and vagina, called an enterocele. Broadly, there are four types based on suspected etiology. Congenital enteroceles are thought to occur because of failure of fusion or reopening of the fused peritoneal leaves down to the perineal body. Posthysterectomy vault prolapses may be "pulsion" types that are caused by pushing with increased intra-abdominal pressure. They may occur because of failure to reapproximate the superior aspects of the pubocervical fascia and the rectovaginal fascia at the time of surgery. Enteroceles that are associated with cystocele and rectocele may be from "traction" or pulling down of the vaginal vault by the prolapsing organs. Finally, iatrogenic prolapses may occur after a surgical procedure that changes the vaginal axis, such as certain surgical procedures for treatment of incontinence. With regard to rectoceles, low rectoceles may result from disruption of connective tissue supports in the distal posterior vaginal wall, perineal membrane, and perineal body. Mid-vaginal and high rectoceles may result from loss of lateral supports or defects in the rectovaginal septum. High rectoceles may result from loss of apical vaginal supports. Posterior or posthysterectomy enteroceles may accompany rectoceles.

Several factors have been implicated as being involved in genital prolapse in women. It is thought that individual women have differing inherent strength of the relevant connective tissue. Further, loss of connective tissue strength might be associated with damage at childbirth, deterioration with age, poor collagen repair mechanisms, and poor nutrition. Loss of muscle strength might be associated with neuromuscular damage during childbirth, neural damage from chronic straining, and metabolic diseases that affect muscle function. Other factors involved in prolapse include increased loads on the supportive system, as seen in prolonged lifting or chronic coughing from chronic pulmonary disease, or some disturbance in the balance of the structural support of the genital organs. Obesity, constipation, and a history of hysterectomy have also been implicated as possible factors.

As noted, vaginal prolapse and the concomitant anterior cystocele can lead to discomfort, urinary incontinence, and incomplete emptying of the bladder. Posterior vaginal prolapse may additionally cause defecatory problems, such as tenesmus and constipation. Furthermore, apart from the physical symptoms, vaginal prolapse has been shown to result in a lower quality of life for its sufferers, including feeling less attractive, less feminine, and less sexually attractive.

Vaginal prolapse develops when intra-abdominal pressure pushes the vagina outside the body. In a normal situation, the levator ani muscles close the pelvic floor. This results in little force being applied to the fascia and ligaments that support the genital organs. Increases in abdominal pressure, failure of the muscles to keep the pelvic floor closed, and damage to the ligaments and fascia all contribute to the development of prolapse. In addition, if a woman has a hysterectomy, the vaginal angle may be altered, causing increased pressure at a more acute angle, accelerating the prolapse.

There are generally two different types of tissue that make up the supportive structure of the vagina and uterus. First, there are fibrous connective tissues that attach these organs to the pelvic walls (cardinal and uterosacral ligaments; pubocervical and rectovaginal fascia). Second, the levator ani muscles close the pelvic floor so the organs can rest on the muscular shelf thereby provided. It is when damage to the muscles opens the pelvic floor or during the trauma of childbirth that the fascia and ligaments are strained. Breaks in the fascia allow the wall of the vagina or cervix to prolapse downward.

As noted above, the levator ani muscles close the pelvic floor so the organs can rest on the muscular shelf thereby provided. The levator ani muscles arise from the pubis, the pelvic fascia, and the ischial spine. They insert on the pelvic viscera, coccyx, and the fibrous raphe of the perineum.

When damage has occurred in the levator muscle, most commonly as a result of obstetric injury, the anatomical defect is noted as a tendency towards a vertical elongation of the levator plate. This downward sagging of the levator plate results in the longitudinal enlargement of the levator hiatus with secondary placement of the cervix and upper vagina upon the levator hiatus. With increased intra-abdominal pressure the defective levator plate is no longer supportive of the downward movement of the uterus, cervix and upper vagina, which are resting upon the levator hiatus, and genital prolapse develops. Over a period of time elongation of the uterosacral and cardinal ligaments will result.

The cardinal and uterosacral ligaments form a suspensory mechanism that suspends the vaginal apex but allows for some vertical mobility. In the normal woman the cervix will descend to but not below the plane of the ischial spines. Damage to the cardinal uterosacral ligament complex permits the uterus and upper vagina to telescope downwards, like an inverted sock. Complete failure of the cardinal uterosacral ligament complex will result in a "cervix-first" prolapse.

Anteriorly, the continence mechanism is maintained by the integrity of the sub-urethral hammock and the insertion of pubo-urethral ligaments into the mid urethra. Posteriorly, the perineal body needs to be firm and substantial in size to allow stretching and angulation of the vagina around it. Levator muscle distension can have a significant effect on perineal body descent and future pelvic prolapse, as well as prolapse recurrence.

Treatment of vaginal prolapse is uncertain, and generally based on the symptoms of the prolapse. If symptoms are more severe, treatment is commonly by either surgery or pessary. Surgical options might include hysterectomy or by uterus-saving procedures. Such procedures may include abdominal or vaginal access routes. Sacralcolpopexy or sacrospinous fixation may be used. Anterior colporrhaphy is often utilized for treatment of anterior vaginal prolapse. In addition, methods of surgical repair using mesh or biological implants, or a combination thereof, to support the prolapsed organ in its appropriate position, have been developed, and may use either a transobturator or vaginal approach.

Traditional anterior prolapse repairs have a relatively high failure rate. Consequently, mesh or grafts have been used to provide additional support for a traditional repair. However, the typical placement of such augmentation of the levator muscle is through a transvaginal approach, with transvaginal dissection. Such transvaginal dissection can be more difficult for the surgeon and may lead to further failures. Consequently, there is a need for alternative methods and apparatus for augmentative support of repaired levator muscle in cases of pelvic organ prolapse.

SUMMARY OF THE INVENTION

The present invention includes surgical instruments and implantable articles for urological applications, particularly levator muscle repair as supportive treatment for other repairs of pelvic organ prolapse, or as a standalone treatment for prolapse.

The present invention comprises placing mesh subcutaneously against the levator muscle, rather than transvaginally, requiring no vaginal dissection in a preffered embodiment.

In a preferred embodiment the mesh apparatus of the present invention is trapezoid-shaped. The mesh is placed surgically bilaterally on each side of the body between the levator muscle and associated fatty tissue. The mesh is placed such that the base of the trapezoid-shaped mesh runs from the obturator to the ischial spine, with the top of the trapezoid tucked under the rectum.

The mesh apparatus is implanted subcutaneously with a novel introducer. The introducer inserts the mesh, spreads it, and opens it in the proper orientation and location. Following such implantation, the mesh apparatus may be secured with sutures or staples in a preferred embodiment.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
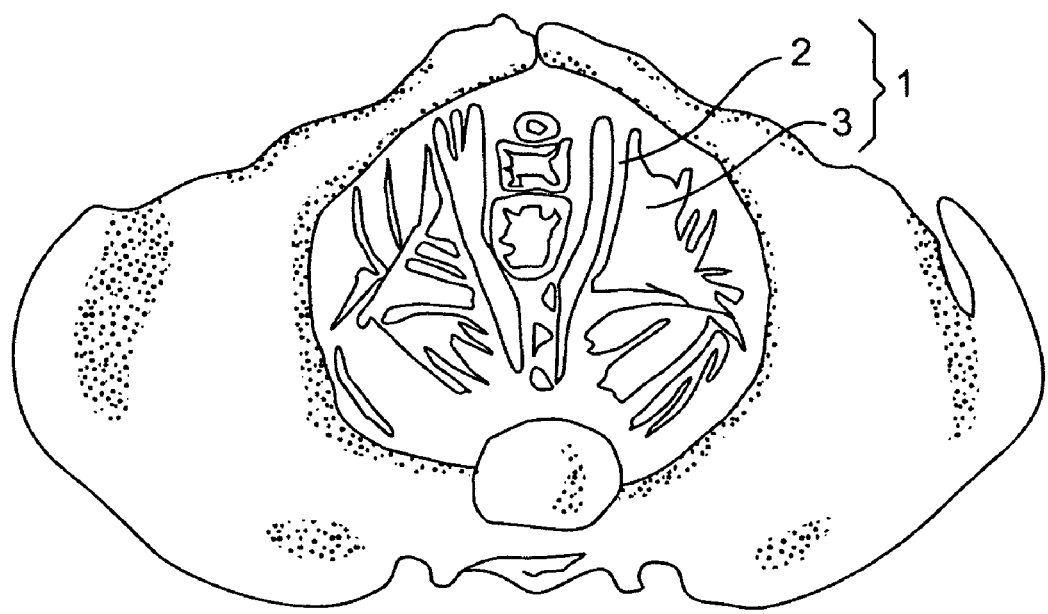
FIG. 1 shows the anatomy of the pelvic floor, including the pubococcygeus muscles and illiococcygeus muscles that make up the levator ani muscles.

Referring now to the drawings, wherein like reference numerals designate identical or corresponding parts throughout the several views. The following description is meant to be illustrative only, and not limiting other embodiments of this invention will be apparent to those of ordinary skill in the art in view of this description.

Figure 2:
FIG. 2 shows a schematic illustrating the general condition of healthy levator muscles.
Figure 3:
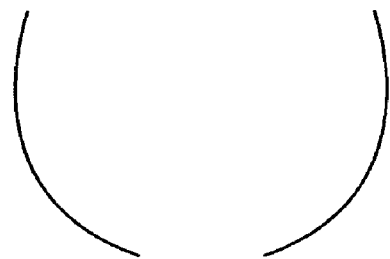
FIG. 3 shows a schematic illustrating the general condition of levators associated with prolapsed pelvic organs.

The relevant anatomy is illustrated in FIG. 1. As can be seen, the levator ani muscles 1, including the pubococcygeus 2 and illiococcygeus muscles 3, are a significant portion of the pelvic floor and provide support for the pelvic viscera. FIGS. 1 and 2 show the normal condition of the levator muscles, while FIG. 3 shows the posture of levator muscles associated with prolapsed pelvic organs. As can be seen, such muscles offer less support for the pelvic viscera and may benefit from additional support as provided in the present invention.

Figure 4:
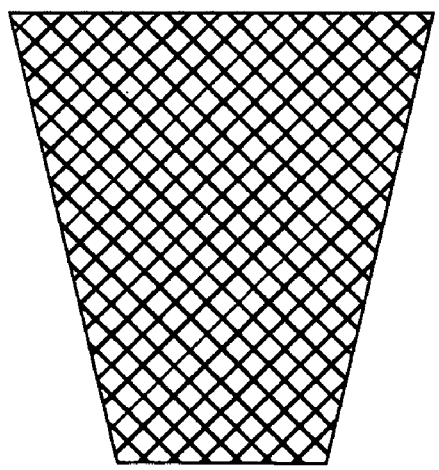
FIG. 4 shows a plan view of the mesh apparatus of the present invention.

In the present invention, the mesh implant, an embodiment which is illustrated in FIG. 4, is placed external to the levator muscles. Such placement reinforces the muscle. Tissue ingrowth during the normal healing process will further support the muscle, and the mesh implant will prevent overdistension of the muscles. It is noted that the top edge of the mesh apparatus can be reinforced with plastic or other similar materials to provide spring and to hold the mesh in the desired shape in vivo, allowing for improved ease in placement. The mesh apparatus may also comprise rivets or some similar palpable marker in certain locations, such as on the corners, in order to provide additional ease and certainty in terms of appropriate placement of the device.

In a preferred embodiment, the mesh implant is placed bilaterally on each side on both the right and left side of the patient's body, and is placed in a subcutaneous location between the levator muscle and the overlying fatty tissue.

Figure 5:
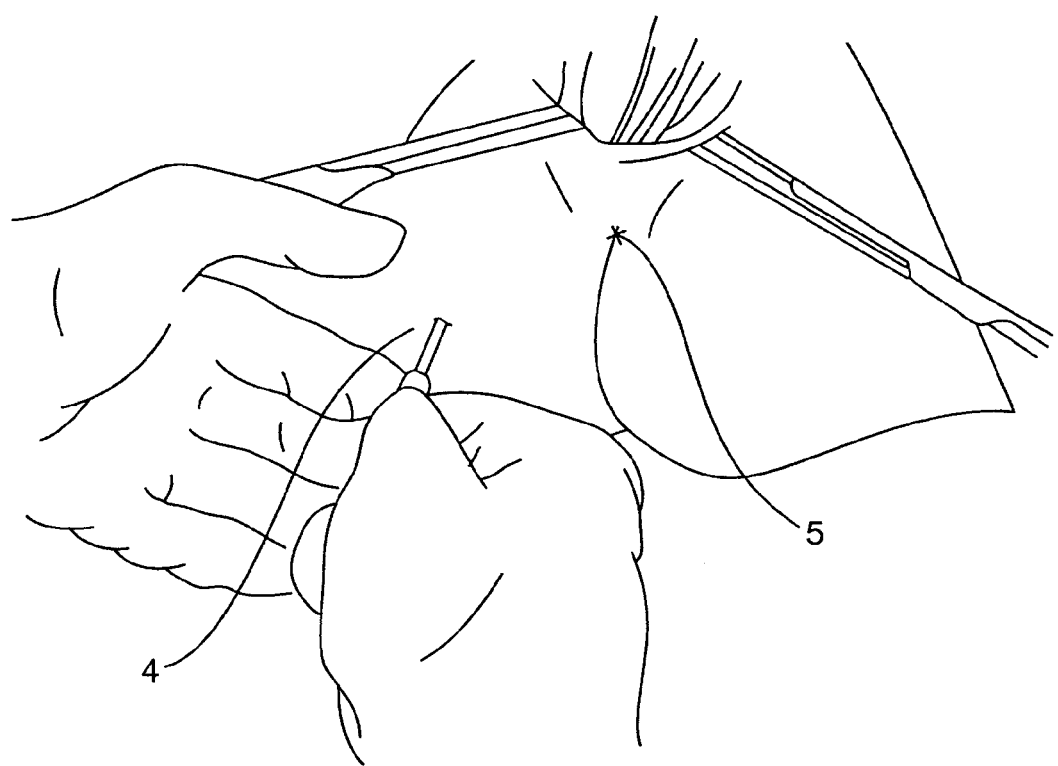
FIG. 5 shows the approximate location of insertion of the mesh of the present invention.
Figure 6:
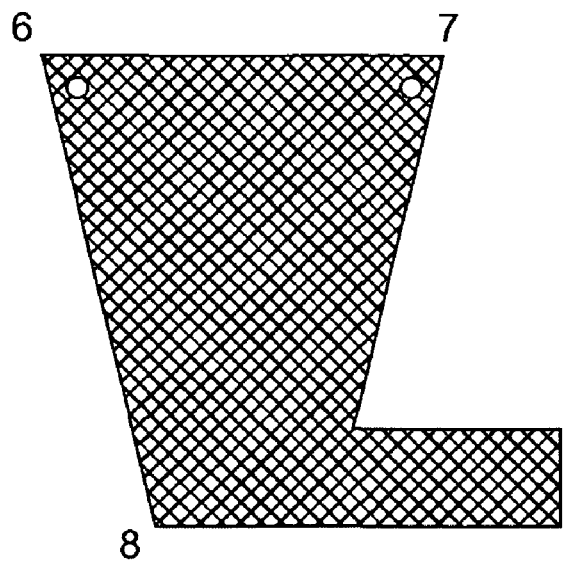
FIG. 6 shows a schematic illustrating the appropriate orientation of the mesh in vivo.

FIG. 5 shows a preferred approximate location of insertion of the mesh apparatus of the present invention. As illustrated, a small incision 4 is made on each side of the rectum approximately 3 cm lateral and 3 cm posterior to the anus 5. Instead of dissecting through the muscle, the surgeon creates a space by bluntly moving along the belly of the muscle to the ischial spine, sweeping off the ischial spine. Another embodiment may use pillow dissection with placement of a balloon device, followed by inflation of such a balloon to create the required space. An example of proper placement is illustrated schematically in FIG. 6. As illustrated, the upper edge of the mesh apparatus runs from the ischial spine 6 to the obturator foramen 7. The lower edge (ie, the base of the trapezoid) is curled under the rectum 8.

Figure 7:
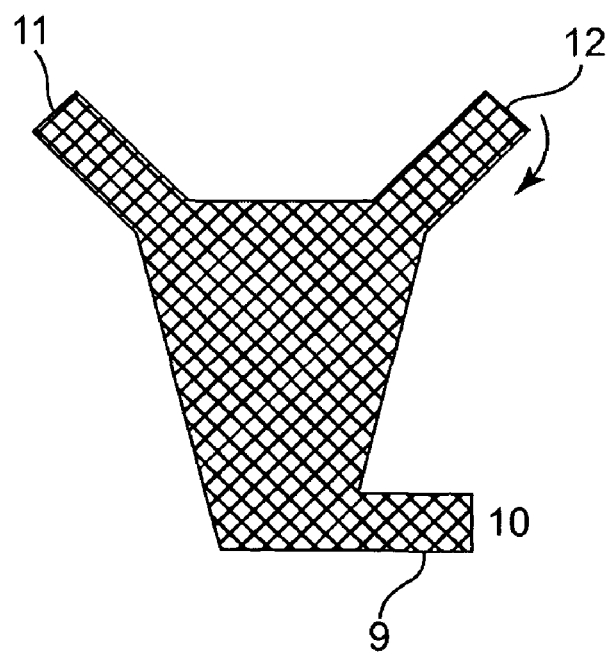
FIG. 7 shows a schematic illustrating an alternative orientation of the mesh in vivo.
Figure 8:
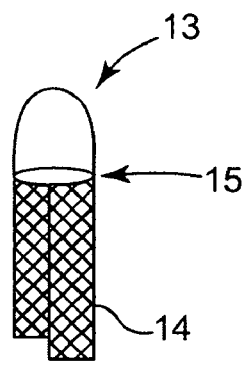
FIGS. 8-13 show an embodiment of an introducer for use in the present invention.
Figure 9:
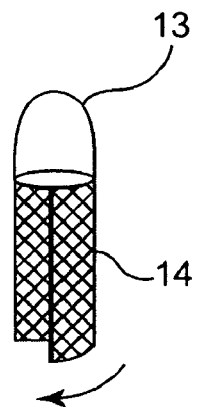
Figure 10:
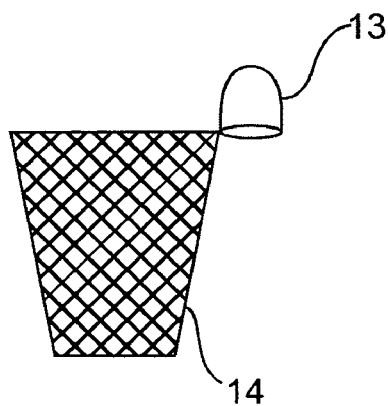
Figure 11:
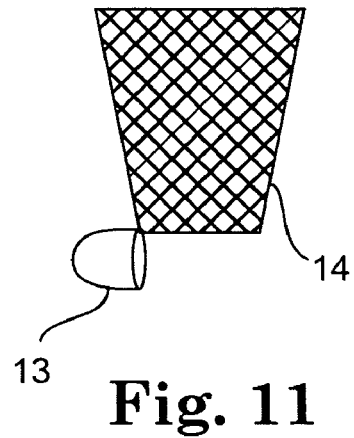

A small tail of mesh 9 can be used to support the perineal body 10 in an embodiment of the present invention. Such placement is illustrated schematically in FIG. 7. FIG. 7 also illustrates an embodiment of the mesh of the present invention in which the upper edge of the mesh comprise arms 11 and 12. These arms allow for transvaginal placement of the mesh as an alternative procedure. Such an alternative may be especially beneficial in instances where the patient is in need of other surgical treatment, such as placement of urethral support devices.

Appropriate insertion devices, or introducers, which allow for correct placement of the described mesh are within the scope of the present invention. Some embodiments are illustrated in FIGS. 8-13 and 14-18, though other embodiments are possible.

Figure 12:
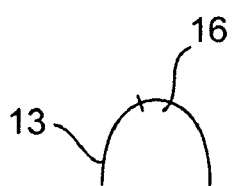
Figure 13:
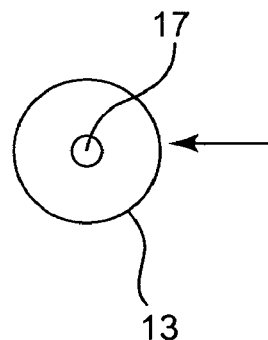
Figure 14:
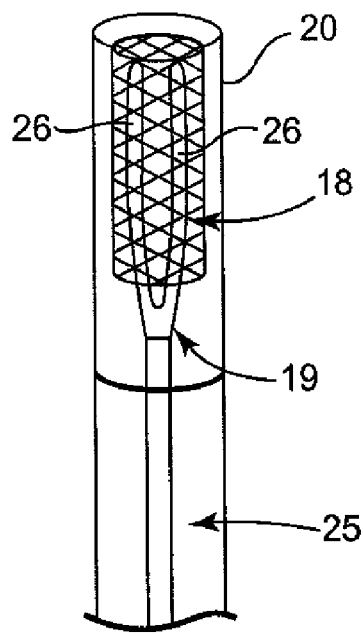
FIGS. 14-18 show an alternative embodiment of an introducer for use in the present invention.

FIGS. 8-13 illustrates embodiments of the introducer of the present invention. These embodiments comprise a thimble tunneling device to which the mesh implant is attached. The thimble portion 13 is inserted via the surgeon's finger. After insertion to the proper location, the attached mesh implant portion 14 is unrolled to its proper orientation. Implant 14 has a top edge and a bottom edge. The top and bottom edges are different lengths and are parallel to each other. Devices to assist in the deployment of the mesh, such as mesh perforations 15, push buttons, needles, or staples are within the scope of the present invention. An example of an embodiment in which the thimble portion comprises a needle 16 is seen in FIG. 12. The needle allows for a small bite of tissue is illustrated to secure placement of the mesh. The thimble may also comprise a button 17, an embodiment of which is illustrated in FIG. 13. In an embodiment, such button could be engaged to release suture or staple to secure the mesh.

Figure 15:
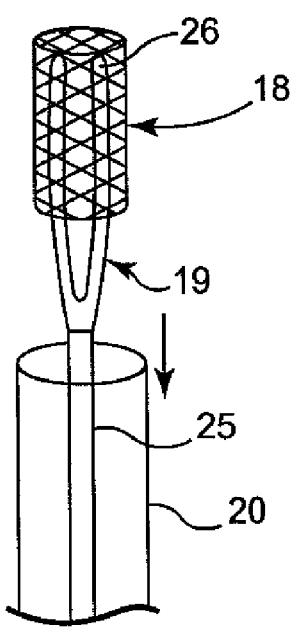
Figure 16:
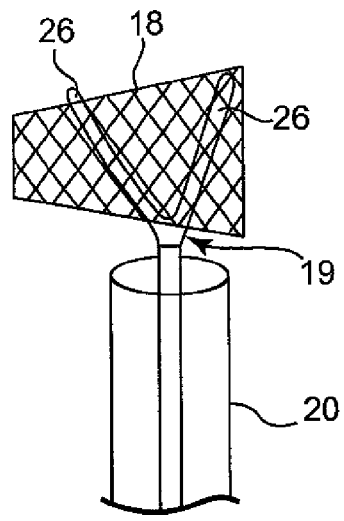
Figure 17:
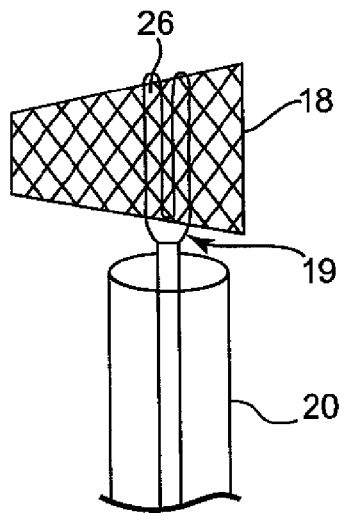
Figure 18:
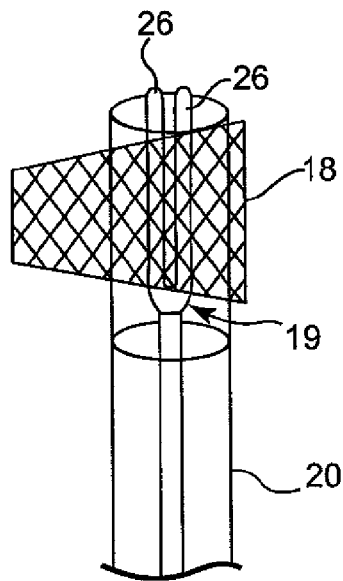
Figure 19:
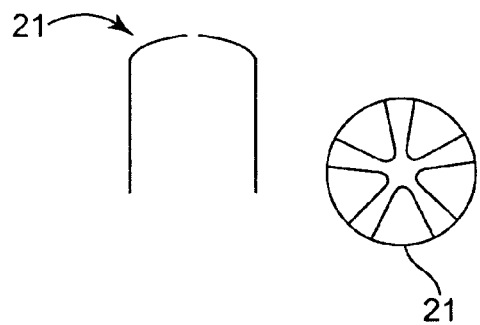
FIG. 19 shows flaps on the leading end of the introducer.

FIGS. 14-18 illustrate another embodiment of the introducer of the present invention. In this embodiment, the mesh apparatus 18 may be rolled around a device 19 having the capability of spreading, with the mesh not attached to the device 19, but covered by a protective sheath 20. As seen in FIG. 15, upon insertion by the surgeon, and appropriate location of the mesh, the protective sheath 20 may be removed. In FIG. 16, the spreaders 26 of device 19 are spread by actuating spreader controls 25, releasing the mesh to its appropriate orientation. The mesh apparatus is then stabilized in its proper location and orientation with staples or tacks, for example. Following such stabilization, the spreaders 26 are retracted to the un-spread condition, as in FIG. 17. The sheath is replaced, as in FIG. 18, and the introducer is withdrawn. Appropriate safety features such as flaps 21 on the leading end of the introducer to prevent catching tissue inadvertently are also within the scope of the present invention, as shown in FIG. 19.

Figure 21:
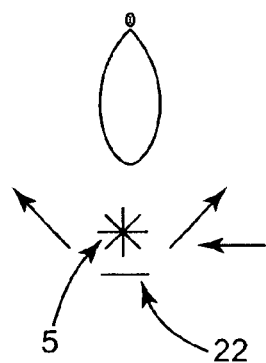
FIG. 21 shows an alternative site of incision for the present invention.

Alternatively, a mesh implant to effect support of distended levator ani muscle may be implanted, as illustrated in FIG. 21, by first making an approximately 3 cm long Krasky incision 22 beginning at a point approximately 2 cm inferior to the anus 5. Following such an incision, the surgeon may bluntly dissect a location for the placement of the mesh implant by inserting a finger into the incision and tunneling toward the ischial spine on the left side of the patient. Using blunt dissection, the surgeon uses his finger to open the space to the spine. In this position, the finger lies in the space between the levator muscle medially and the fatty tissue laterally. By making a sweeping motion with his finger, the surgeon creates a space, until both the ischial spine and the inferior pubic ramus are palpable.

Figure 20:
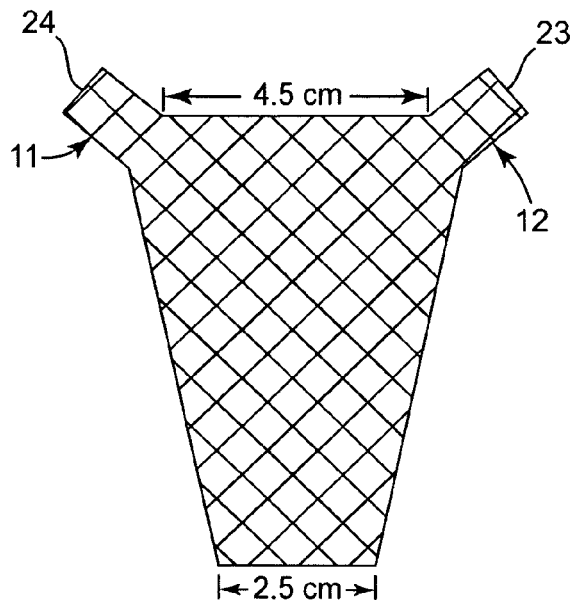
FIG. 20 shows an alternative embodiment of the mesh placement of the present invention.

Following creating of the space by blunt dissection, the mesh can be placed with a needle in an embodiment of the present invention. The needle may be inserted through an anchor 23,24 or other tissue fixation structure disposed on an arm 11,12 on the mesh, as illustrated in FIG. 20. The surgeon places his finger on the ischial spine, then runs the needle along his finger until the end of the anchor pushes into the tissue, which will be adjacent the ischial spine in the levator muscle (i.e, at the sacrospinous ligament, the ischiorectal fossa, or the illiococcygeus muscle). The anchor engages the tissue at this point, and the needle is removed by withdrawing from the incision. The needle is then inserted into an anchor or other tissue fixation structure on the other arm of the mesh implant. The surgeon then places his finger on the pubic ramus, runs the needle along his finger, thereby pushing the anchor into the obturator internus muscle, engaging that tissue. The needle is removed by withdrawing from the incision. The surgeon then sweeps along the mesh, smoothing the area between the anchors and sweeping the tail end of the mesh beneath the rectum.

The dissection and mesh placement is repeated on the right side of the patient. The tail ends of the two implants may overlap beneath the rectum or anococcygeal body following placement, or may be sutured together. Following placement of the mesh implants, the Krasky incision is closed.

Obviously, numerous modifications and variations of the present invention are possible in light of the above teachings. It is therefore to be understood that within the scope of the appended claims, the invention may be practiced otherwise than as specifically described herein for both female and male patients.

The invention claimed is:

1. A surgical kit for the treatment of pelvic organ prolapse, said kit comprising:
   a. an implant comprising a mesh portion having a trapezoidal shape having a top edge and a bottom edge opposite said top edge, wherein the top and bottom edges are different lengths and are parallel to each other; and
   b. an introducer for placement of the implant in an appropriate anatomical location, wherein the introducer comprises a thimble portion detachably connected to the mesh portion;
   wherein the implant includes an insertion configuration in which the implant is rolled relative to the thimble portion and a deployed configuration in which the implant is unrolled relative to the thimble portion.

2. The kit of claim 1, wherein said implant comprises at least one arm adjacent the top edge of said mesh portion.

3. The kit of claim 2, wherein said at least one arm comprises a tissue fixation mechanism.

4. The kit of claim 3, wherein said tissue fixation mechanism comprises an anchor.

5. The kit of claim 1, wherein said implant comprises a tail of mesh adjacent a bottom edge of said mesh portion.

6. The kit of claim 1, wherein said implant comprises rivets or other palpable structures located at the corners of said mesh portion.

7. The kit of claim 1, wherein said top edge of said mesh portion is reinforced with plastic.

8. The surgical kit of claim 1, wherein the mesh portion comprises perforations to facilitate detachment of the implant from the thimble portion.

9. The surgical kit of claim 1, wherein the thimble portion comprises a needle.

10. The surgical kit of claim 1, wherein the thimble portion comprises a push button mechanism adapted to deploy the implant.

11. The surgical kit of claim 1, wherein the introducer comprises a spreader device comprising an outer surface about which said implant may be rolled when the spreader device is in its unspread condition.

12. The surgical kit of claim 11, further comprising a protective sheath covering said implant rolled about said spreader device in its unspread condition.

13. The surgical kit of claim 11, wherein said introducer comprises a control mechanism adapted to adjust said spreader device from an unspread condition to a spread condition.

14. The surgical kit of claim 11, wherein the spreader device comprises multiple spreaders that are spreadable and retractable relative to each other.

* * * * *